(12) United States Patent
Sagar et al.

(10) Patent No.: US 10,378,006 B2
(45) Date of Patent: Aug. 13, 2019

(54) NEAR-INFRARED RAY EXPOSURE SYSTEM FOR BIOLOGICAL STUDIES

(71) Applicants: Vidya Sagar, Miami, FL (US); Madhavan Nair, Coral Gables, FL (US)

(72) Inventors: Vidya Sagar, Miami, FL (US); Madhavan Nair, Coral Gables, FL (US)

(73) Assignee: The Florida International University Board of Trustees, Miami, FL (US)

( * ) Notice: Subject to any disclaimer, the term of this patent is extended or adjusted under 35 U.S.C. 154(b) by 0 days.

(21) Appl. No.: 15/491,137

(22) Filed: Apr. 19, 2017

(65) Prior Publication Data
US 2018/0305679 A1    Oct. 25, 2018

(51) Int. Cl.
| | | |
|---|---|---|
| *C12N 13/00* | (2006.01) | |
| *G01N 21/359* | (2014.01) | |
| *G01N 21/17* | (2006.01) | |
| *G02B 21/26* | (2006.01) | |
| *H04N 5/33* | (2006.01) | |
| *G02B 21/06* | (2006.01) | |
| *G02B 21/36* | (2006.01) | |
| *G01N 15/14* | (2006.01) | |
| *G02B 21/00* | (2006.01) | |
| *G01N 15/10* | (2006.01) | |

(52) U.S. Cl.
CPC ......... *C12N 13/00* (2013.01); *G01N 15/1468* (2013.01); *G02B 21/0076* (2013.01); *G02B 21/06* (2013.01); *G02B 21/26* (2013.01); *G02B 21/367* (2013.01); *G01N 2015/1006* (2013.01)

(58) Field of Classification Search
None
See application file for complete search history.

(56) References Cited

U.S. PATENT DOCUMENTS

| | | | | |
|---|---|---|---|---|
| 4,888,463 | A * | 12/1989 | Middlebrook | B01L 7/00 219/201 |
| 5,818,582 | A | 10/1998 | Fernandez et al. | |
| 5,865,754 | A | 2/1999 | Sevick-Muraca et al. | |
| 6,415,236 | B2 | 7/2002 | Kobayashi et al. | |
| 6,449,039 | B1 | 9/2002 | Bouzid | |
| 7,061,606 | B2 * | 6/2006 | Treado | G01J 3/2823 250/330 |
| 2004/0061073 | A1 | 4/2004 | Kitagawa | |
| 2007/0053388 | A1 | 3/2007 | Mizuuchi | |
| 2007/0078310 | A1 | 4/2007 | Lee et al. | |
| 2008/0160090 | A1 | 7/2008 | Oraevsky et al. | |
| 2009/0254154 | A1 * | 10/2009 | De Taboada | A61N 5/0613 607/88 |
| 2011/0267681 | A1 | 11/2011 | Gerbier et al. | |
| 2012/0032147 | A1 | 2/2012 | Nagai et al. | |
| 2017/0096659 | A1 * | 4/2017 | Ghosh | C12N 13/00 |

OTHER PUBLICATIONS

Di Corato (Combining Magnetic Hyperthermia and Photodynamic Therapy for Tumor Ablation with Photoresponsive Magnetic Liposomes, 2015). (Year: 2015).*
Gu et al., "Crystalline magnetic carbon nanoparticle assisted photothermal delivery into cells using CW near-infrared laser beam," Scientific Reports, May 29, 2014, pp. 1-10, vol. 4, No. 5106.
Wang et al., "Magnetic/NIR-responsive drug carrier, multicolor cell imaging, and enhanced photothermal therapy of gold capped magnetite-fluorescent carbon hybrid nanoparticles," Nanoscale, Mar. 23, 2015, pp. 7885-7895.
Maier-Hauff et al., "Efficacy and safety of intratumoral thermotherapy using magnetic iron-oxide nanoparticles combined with external beam radiotherapy on patients with recurrent glioblastoma multiforme," Journal of Neuro-Oncology, Jun. 2011, pp. 317-324, vol. 103.
Yan et al., "Near infrared light triggered release of biomacromolecules from hydrogels loaded with upconversion nanoparticles," Journal of the American Chemical Society, Sep. 26, 2012, pp. 16558-16561, vol. 134.
You et al., "Near-infrared light sensitive liposomes for the enhanced photothermal tumor treatment by the combination with chemotherapy," Pharmaceutical Research, Mar. 2014, pp. 554-565, vol. 31, No. 3, Author Manuscript.
Chu et al., "Near-infrared laser light mediated cancer therapy by photothermal effect of Fe3O4 magnetic nanoparticles," Biomaterials, May 2013, pp. 4078-4088, vol. 34.
Sagar et al., "Towards nanomedicines for neuroAIDS," Reviews in Medical Virology, Jan. 7, 2014, pp. 103-124, vol. 24.
Santoso et al., "Magnetic nanoparticles for targeting and imaging of stem cells in myocardial infarction," Stem Cells International, Feb. 2016, pp. 1-9.
Laurent et al., "Superparamagnetic iron oxide nanoparticles for delivery of therapeutic agents: opportunities and challenges," Expert Opinion on Drug Delivery, Sep. 2014, pp. 1-22, vol. 11, No. 9.
Long et al., "Biomedical applications of advanced multifunctional magnetic nanoparticles," Journal of Nanoscience and Nanotechnology, Dec. 2015, pp. 10091-10107, vol. 15, No. 12.
Benede et al., "Development of stir bar sorptive-dispersive microextraction mediated by magnetic nanoparticles and its analytical application to the determination of hydrophobic organic compounds in aqueous media," Journal of Chromatography A, Oct. 2014, pp. 25-33, vol. 1362.

(Continued)

*Primary Examiner* — Nghi V Nguyen
(74) *Attorney, Agent, or Firm* — Saliwanchik, Lloyd & Eisenschenk

(57) ABSTRACT

An apparatus and methods of using the same for conducting photonic and optical treatments on biological samples with additional functions including temperature monitoring and real-time microscopic imaging are provided. The photonic and optical treatments can be conducted using light with wavelengths in the near-infrared region (NIR) on biological samples, including in-vitro brain cell cultures, in-vivo central nervous system (CNS) and peripheral nervous system (PNS) tissue samples, and other body tissues. The apparatus and methods can be combined with magnetic nanoparticles treatment to accomplish non-invasive, on-demand drug targeting, brain cell specific gene delivery, and magnetized photo-biomodulation for treating various CNS disorders.

6 Claims, 5 Drawing Sheets

(56) References Cited

OTHER PUBLICATIONS

Sagar et al., "Therapeutical neurotargeting via magnetic nanocarrier: implications to opiate-induced neuropathogenesis and neuroAIDS," Journal of Biomedical Nanotechnology, Oct. 2015, pp. 1-12, vol. 11.
Ding et al., "Enhanced blood-brain barrier transmigration using a novel transferrin-embedded fluorescent magnetoliposome nanoformulation," Nanotechnology, Feb. 2014, pp. 1-30, vol. 25, No. 5, Author Manuscript.
Shen et al., "Magnetic nanoparticle clusters for photothermal therapy with near-infrared irradiation," Biomaterials, Jan. 2015, pp. 67-74, vol. 39.
Jain et al., "Biodistribution, clearance, and biocompatibility of iron oxide magnetic nanoparticles in rats," Molecular Pharmaceutics, Jan. 25, 2008, pp. 316-327, vol. 5, No. 2.
Mura et al., "Stimuli-responsive nanocarriers for drug delivery," Nature Materials, Nov. 2013, pp. 991-1003, vol. 12.
Reineke, "Stimuli-responsive polymers for biological detection and delivery," ACS Macro Letters, Dec. 9, 2015, pp. 14-18, vol. 5.
Medeiros et al., "Stimuli-responsive magnetic particles for biomedical applications," International Journal of Pharmaceutics, Jan. 2011, pp. 139-161, vol. 403.
Tao et al., "Direct gene transfer into human cultured cells facilitated by laser micropuncture of the cell membrane," Proceedings of the National Academy of Sciences of the United States of America, Jun. 1987, pp. 4180-4184, vol. 84.
Schneckenburger et al., "Laser-assisted optoporation of single cells," Journal of Biomedical Optics, Jul. 2002, pp. 410-416, vol. 7, No. 3.
Mohanty et al., "Laser-assisted microinjection into targeted animal cells," Biotechnology Letters, Jun. 2003, pp. 895-899, vol. 25.
Hosokawa et al., "Gene delivery process in a single animal cell after femtosecond laser microinjection," Applied Surface Science, Sep. 2009, pp. 9880-9884, vol. 255.
Sordillo et al., "Deep optical imaging of tissue using the second and third near infrared spectral windows," Journal of Biomedical Optics, May 2014, pp. 056004-1-056004-6, vol. 19, No. 5.
Tirlapur et al., "Targeted transfection by femtosecond laser," Nature, Jul. 18, 2002, pp. 290-291, vol. 418.
Hergt et al., "Magnetic particle hyperthermia: nanoparticle magnetism and materials development for cancer therapy," Journal of Physics: Condensed Matter, Sep. 2006, pp. S2919-S2934, vol. 18.
Tang et al., "Combined effects of laser-ICG photothermotherapy and doxorubicin chemotherapy on ovarian cancer cells," Journal of Photochemistry and Photobiology B: Biology, Dec. 2009, pp. 138-144, vol. 97.
Pilakka-Kanthikeel et al., "Targeted brain derived neurotropic factors (BDNF) delivery across the blood-brain barrier for neuroprotection using magnetic nano carriers: an in-vitro study," PLOS One, Apr. 2013, pp. 1-10, vol. 8, No. 4.
Atluri et al., "Vorinostat positively regulates synaptic plasticity genes expression and spine density in HIV infected neurons: role of nicotine in progression of HIV-associated neurocognitive disorder," Molecular Brain, May 2014, pp. 1-17, vol. 7, No. 37.
Liu et al.,"Voyage inside the cell: microsystems and nanoengineering for intracellular measurement and manipulation," Microsystems and Nanoengineering, Sep. 2015, pp. 1-15, vol. 1, No. 15020.

Saiyed et al., "Magnetic nanoformulation of azidothymidine 5'-triphosphate for targeted delivery across the blood-brain barrier," International Journal of Nanomedicine, Apr. 2010, pp. 157-166, vol. 5.
Shi et al., "Photo-fluorescent and magnetic properties of iron oxide nanoparticles for biomedical applications," Nanoscale, Apr. 2015, pp. 1-24.
Zhu et al., "Photothermally sensitive poly(N-isopropylacrylamide)/graphene oxide nanocomposite hydrogels as remote light-controlled liquid microvalves," Advanced Functional Materials, Jun. 2012, pp. 4017-4022, vol. 22.
Fusco et al., "An integrated microrobotic platform for on-demand targeted therapeutic interventions," Advanced Materials, Feb. 2014, pp. 952-957, vol. 26.
Hofmann-Amtenbrink et al., "Superparamagnetic nanoparticles for biomedical applications," Nanostructured Materials for Biomedical Applications, Jan. 2009, pp. 119-149.
Parton et al., "Biomedical applications using magnetic nanoparticles," Solid State Technology, 2008, pp. 1-9.
Unsoy et al., "Targeted silencing of survivin in cancer cells by siRNA loaded chitosan magnetic nanoparticles," Expert Review of Anticancer Therapy, May 2016, pp. 789-797, vol. 16, No. 7.
Valdiglesias et al., "Are iron oxide nanoparticles safe? Current knowledge and future perspectives," Journal of Trace Elements in Medicine and Biology, Dec. 2016, pp. 53-63, vol. 38.
Wiogo et al., "Insight into serum protein interactions with functionalized magnetic nanoparticles in biological media," Langmuir, Feb. 2012, pp. 4346-4356, vol. 28.
Ghose et al., "Surface structure and reactivity of iron oxide-water interfaces," Developments in Earth and Environmental Sciences, Apr. 2008, pp. 1-32, vol. 7.
Bansal et al., "Photocontrolled nanoparticle delivery systems for biomedical applications," Accounts of Chemical Research, Aug. 2014, pp. 3052-3060, vol. 47.
Kim et al., "Near-infrared light-responsive nanomaterials for cancer theranostics," WIREs Nanomedicine and Nanobiotechnology, Jan./Feb. 2016, pp. 23-45, vol. 8.
Palumbo et al., "Targeted gene transfer in eucaryotic cells by dye-assisted laser optoporation," Journal of Photochemistry and Photobiology B: Biology, Oct. 1996, pp. 41-46, vol. 36.
Liu et al., "Functional nanomaterials for near-infrared-triggered cancer therapy," Biomaterials Science, Mar. 2016, pp. 1-20.
Stracke et al., "Optical nanoinjection of macromolecules into vital cells," Journal of Photochemistry and Photobiology B: Biology, Sep. 2005, pp. 136-142, vol. 81.
Schinkel et al., "Infrared picosecond laser for perforation of single plant cells," Biotechnology and Bioengineering, Jan. 2008, pp. 244-248, vol. 99, No. 1.
Hondroulis et al., "Impedance based nanotoxicity assessment of graphene nanomaterials at the cellular and tissue level," Analytical Letters, Feb. 2012, pp. 272-282, vol. 45.
Sun et al., "Synthesis of nanometer-size maghemite particles from magnetite," Colloids and Surfaces A: Physicochemical and Engineering Aspects, Sep. 2004, pp. 15-19, vol. 245.
Hondroulis et al., "Whole cell based electrical impedance sensing approach for a rapid nanotoxicity assay," Nanotechnology, Jul. 2010, pp. 1-9, vol. 21.

* cited by examiner

NEAR-INFRARED RAY EXPOSURE SYSTEM FOR BIOLOGICAL STUDIES

GOVERNMENT SUPPORT

This invention was made with government support under Grant Nos. DA027049, DA037838, and MH085259 awarded by the National Institutes of Health. The government has certain rights in the invention.

BACKGROUND

Laser-initiated photo-targeting have shown tremendous potential for applications such as, for example, cancer therapy, gene delivery, imaging, and on-demand drug delivery. However, light (e.g., in the ultra-violet (UV)-visible spectral range) potentiates damage to biological subjects such as, for example, cellular organelles, deoxyribonucleic acid (DNA), and proteins. Moreover, UV-visible wavelength does not penetrate deeply enough into tissues or organs in-vivo due to high scattering and absorption.

Recently, near-infrared region (NIR) light has been experimented for several biological applications due to advantages such as minimal absorption, minimal scattering, and deeper penetration in-vivo. NIR light beams with different energy levels (i.e., wavelengths) applied for various duration of time have been used to investigate different biological functions and processes such as, for example, stimulation of light-sensitive polymers, in-vitro microinjection of single cells (requiring low-energy NIR radiation for as little as femtoseconds) and cancer therapy (requiring NIR irradiation for more than 15 minutes).

BRIEF SUMMARY

Photonic irradiation, near-infrared (NIR) irradiation in particular, applied in conjunction with nanoparticles has been employed in treating cancer or other diseases. The application of NIR-based cancer therapy in treating central nervous system (CNS; i.e., the brain), on the other hand, remains a challenge due to the sophistication and interdependence of the brain's cellular networks and the difficulty in minimizing or avoiding damaging thermal effects on the brain cells. As such, there remains a need for simultaneously applying a photonic irradiation source and optically evaluating its thermal effects on brain cells and/or other tissues in one integrated platform.

Embodiments of the subject invention provide apparatuses, as well as methods of using an apparatus, for conducting photonic and optical treatments on biological samples with additional functions including real-time microscopic imaging and temperature monitoring. In some embodiments, the photonic and optical treatments can be conducted using light with wavelengths in the near-infrared region (NIR) on biological samples.

Advantageously, the integrated photonic and optical apparatus of embodiments of the subject invention can be combined with treatments involving nanoparticles such as, for example, magnetic nanoparticles (MNPs), thus enabling applications such as, for example, imaging and on-demand drug targeting, brain cell specific gene delivery, and magnetized photo-biomodulation for treating various nervous system disorders.

BRIEF DESCRIPTION OF THE DRAWINGS

FIG. 8A shows an XRD spectrum of <20 nm MNPs (inset: transmission electron microscopy (TEM) image of the MNPs) showing magnetite-specific characteristics plane. FIG. 8B is a dynamic laser scattering (DLS) measurement of hydrodynamic size distribution of MNPs showing the average colloidal size of nanoparticles as approximately 127 nm. FIG. 8C shows a magnetic hysteresis loop of MNPs showing superparamagnetism, i.e., zero coercivity, at room temperature.

DETAILED DESCRIPTION

Figure 1:
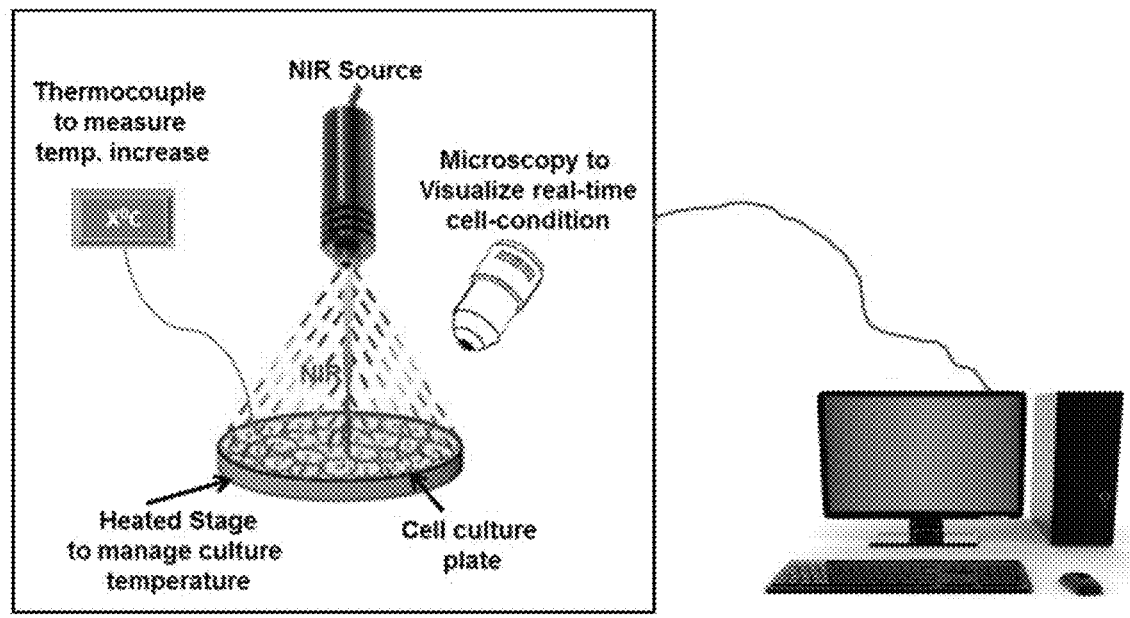
FIG. 1 is a schematic of an exemplary integrated NIR laser apparatus.

Embodiments of the subject invention provide apparatuses, as well as methods of using the apparatuses, for conducting photonic treatments on biological samples with additional functions including temperature monitoring and real-time microscopic imaging.

In an embodiment, an integrated photonic and optical apparatus can comprise a light source, a sample stage located directly beneath the light source capable of fixing the sample thereon and adjusting and/or maintaining the temperature of the sample, and a microscope apparatus optionally accompanied by appropriate hardware and software capable of capturing and generating real-time images of the sample prior to, during, and following it being irradiated by the light source. In some embodiments, the light source and the microscope apparatus are connected via an optical fiber. Optionally, the integrated photonic and optical apparatus comprises a temperature-sensing device capable of monitoring the temperature of the sample. Advantageously, the components of the photonic apparatus can be accommodated in a single housing in a compact design for ease of assembly and transportation.

In some embodiments, the photonic treatments are conducted using light with wavelengths in the near-infrared region (NIR) on biological samples including, but not limited to, cell cultures and tissue samples. Light of other wavelengths can also be used as the source for conducting photonic treatments such as, for example, ionizing radiations (e.g., gamma rays and X-rays). In addition, microwaves and radio waves of various lengths can also be used in embodiments provided herein. Advantageously, the NIR sources provided herein can comprise multiple ranges of wavelength and can be operated in either an intermittent or a continuous mode, allowing a wide range of samples to be examined without causing photonic and optical damage to the sample.

As used herein, the term "NIR light" describes light with wavelengths in the range of 700 nm to 3000 nm. Preferably, the NIR light is in the range of 700 nm to 1000 nm, also known as the "biological window" of wavelengths. In certain embodiments, the NIR light has a wavelength of 808 nm or about 808 nm. The principal advantages of NIR light over UV and visible light is its ability to penetrate deeply into biological tissues (e.g., on the order of centimeters) and a lack of cytotoxicity. In some embodiments, the NIR light source is a semiconductor laser diode. In a particular embodiment, the NIR light is provided by a collimated laser diode and has a power density of about 1.5 $W/cm^2$. However, any power density in the range between about 1 $W/cm^2$ and about 100 $W/cm^2$, preferably between about 1 $W/cm^2$ and about 10 $W/cm^2$, is acceptable in the embodiments provided herein.

In some embodiments, the biological samples provided herein include in-vitro cell culture comprising central nervous system (CNS) cells such as, for example, human primary astrocytes, SK-N-MC human neuroepithelioma cells, and CHME-5 human microglia cells, as well as peripheral nervous system (PNS) cells and other body cell types (e.g., for example, liver cells, lung cells, blood cells). In some embodiments, the biological samples are in-vitro CNS tissues harvested from a subject. The term "subject" as used herein means a human, a non-human mammal (e.g., a dog, a cat, a mouse, a rat, a cow, a sheep, a pig, a goat), a non-human primate, or any other vertebrate. In further embodiments, the integrated NIR photonic and optical apparatus provided herein can be used to treat samples in vivo.

In some embodiments, the microscope apparatus provided herein is capable of capturing real-time images of biological samples as they undergo photonic and optical treatments. The choice of microscope depends upon specific parameters of the samples needing to be monitored. Non-limiting examples of the microscope include electron microscope (e.g., scanning electron microscope, transmission electron microscope, scanning transmission microscope, etc.), laser scanning microscope (e.g., confocal laser scanning microscope), and scanning probe microscope (e.g., atomic force microscope, chemical force microscope, etc.). In certain embodiments, the NIR light can serve as the incident light of the microscope apparatus. In further embodiments, the microscope apparatus is connected with electronic hardware (e.g., computer processors and monitors, etc.) as well as accompanying software (e.g., image-processing software systems, etc.) for real-time image acquisition and processing.

In some embodiments, the integrated photonic and optical apparatus optionally comprises a temperature-sensing device used to measure the temperature of the sample stage, as the sample stage, in some embodiments, can adjust and/or maintain the temperature of the sample (e.g., cell culture and tissue) during the NIR treatment. The sensing device can be any suitable sensor including, but not limited to, a thermometer, a thermistor, and a thermocouple, provided that the device can be connected to the sample stage on which the sample is fixed. In some embodiments, the device is a thermocouple comprising two dissimilar conductors capable of generating different voltage in response to changes in temperatures. Non-limiting examples of thermocouples that can be employed include nickel-alloy based type E, J, K, M, N, and T thermocouples, platinum/rhodium-alloy based type B, R, and S thermocouples, tungsten/rhenium-alloy based type C, D, and G thermocouples, and other types of thermocouples comprising noble metals such as, for example, gold, iron, and platinum.

In another aspect, the integrated photonic and optical apparatus provided herein can be used in combination with technology involving nanoparticles to treat biological samples, preferably brain cells in vitro or CNS tissues in vivo, in a non-invasive manner. In some embodiments, the nanoparticles are magnetic nanoparticles (MNPs). In certain embodiments, other types of nanoparticles and/or nanocarriers can also be used in combination with the NIR apparatus including, for example, gold nanoparticles, silver nanoparticles, palladium and metal chalcogenide nanoparticles, carbon nanotubes, graphene oxide nanoparticles, up-conversion nanocarriers, polymeric nanocarriers, liposomes).

In some embodiments, the MNPs have diameters in the range between about 10 nm and about 1 μm. Further embodiments provide that the colloidal-sized MNPs are between about 100 nm and about 150 nm in size.

In some embodiments, the biological samples are treated with nanoparticles (e.g., MNPs) that are optionally conjugated with one or more drugs or active agents and further encapsulated by materials (e.g., polymers and liposomes) sensitive to NIR light stimulation, such that the application of an integrated NIR photonic and optical treatment can release the MNPs from their encapsulation. This is advantageous because encapsulation by light-sensitive material can prevent nanoparticles-bound drugs from being directly exposed to phagocytic cells of the reticuloendothelial system (RES) as well as other detrimental enzymatic activity in blood circulation in order to significantly improve the physiological bioavailability of drugs or active agents.

In some embodiments, the light-sensitive material is selected from liposomes, hydrogels, fluorescent carbon dots, and a matrix of upconversion materials such as erbium or thulium, etc., which can emit different colored fluorescent lights depending on the wavelength of the light applied. This is a particularly advantageous feature of the subject invention as it allows the combined photonic treatment and nanoparticle delivery to be used in applications such as multi-color imaging modalities (Haro-Gonzalez, P. et al. Optical trapping of $NaYF_4:Er^{3+},Yb^{3+}$ upconverting fluorescent nanoparticles. Nanoscale 5, 12192-12199 (2013)).

The terms "drug" and "active agent," as used in the present application, include any natural or synthetic substance that has a physiological or diagnostic effect when administered to a subject such as, for example, a human or an animal. As used herein, the terms "drug" and "active agent" include therapeutic and diagnostic agents. The drug or active agent can be suitably employed in accordance with the invention with animals, particularly mammals including humans, veterinarian animals and farm animals. Drugs and active agents used in accordance with the subject invention can include those affecting, acting on, or being visualized at a desired target within, or on, the animal body, such as, for example, within the nervous system, including tumor tissue located therein.

In an embodiment, short-term NIR exposure in combination with the use of MNPs can be employed for effective gene delivery, imaging, and controlled drug delivery (Gu, L., Koymen, A. R. & Mohanty, S. K. Crystalline magnetic carbon nanoparticle assisted photothermal delivery into cells using CW near-infrared laser beam. Scientific Reports 4, 5106 (2014); Wang, H. et al. Magnetic/NIR-responsive drug carrier, multicolor cell imaging, and enhanced photothermal therapy of gold capped magnetite-fluorescent carbon hybrid nanoparticles. Nanoscale 7, 7885-7895 (2015)).

In some embodiments, the cytotoxic effect of NIR phototargeting in the presence of MNPs depends on the duration and dose of NIR exposure and the density of nanoparticle clusters (Gu, L., Koymen, A. R. & Mohanty, S. K. Crystalline magnetic carbon nanoparticle assisted photothermal delivery into cells using CW near-infrared laser beam. Scientific Reports 4, 5106 (2014); Maier-Hauff, K. et al. Efficacy and safety of intratumoral thermotherapy using magnetic iron-oxide nanoparticles combined with external beam radiotherapy on patients with recurrent glioblastoma multiforme. Journal of Neuro-Oncology 103, 317-324 (2011); Chu, M. et al. Near-infrared laser light mediated cancer therapy by photothermal effect of $Fe_3O_4$ magnetic nanoparticles. Biomaterials 34, 4078-4088 (2013); Shi, D., Sadat, M. E., Dunn, A. W. & Mast, D. B. Photo-fluorescent and magnetic properties of iron oxide nanoparticles for biomedical applications. Nanoscale 7, 8209-8232 (2015)). Studies suggest that in-vivo cytotoxic effects due to hyperthermia are exerted only when NIR with higher power (>3 $W/m^2$) is exposed for several minutes on a daily basis for several weeks in the presence of MNPs (Shi, D., Sadat, M. E., Dunn, A. W. & Mast, D. B. Photo-fluorescent and magnetic properties of iron oxide nanoparticles for biomedical applications. Nanoscale 7, 8209-8232 (2015)).

As a result, some embodiments provide that the duration of NIR photonic and optical treatment to a cell culture, with or without prior MNP treatment, is limited to between about 1 minute and about 15 minutes, preferably 2 minutes (Chu, M. et al. Near-infrared laser light mediated cancer therapy by photothermal effect of Fe3O4 magnetic nanoparticles. Biomaterials 34, 4078-4088 (2013)).

Figure 7:
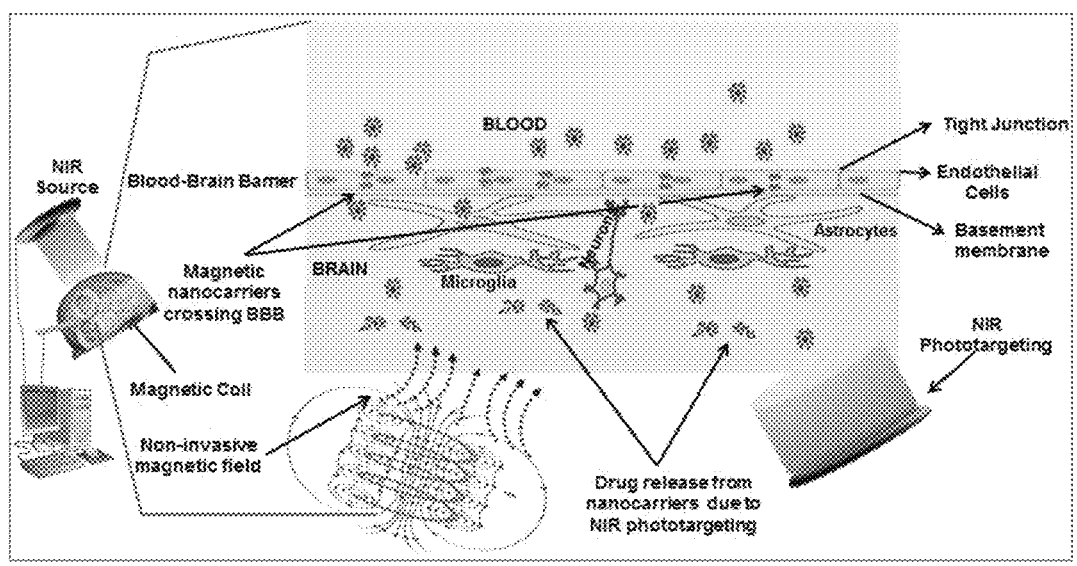
FIG. 7 illustrates an exemplary mechanism for efficacious targeting, delivery, release, and monitoring of therapeutics delivered to the CNS using transient integrated NIR photonic and optical apparatus combined with MNPs treatment. The exemplary NIR photonic apparatus can also be used in combination with other nanocarrier systems.

A person skilled in the art would immediately recognize that no NIR apparatus to date is capable of simultaneously monitoring real-time changes in temperature and morphology of cells, an advantageous feature of the apparatus as provided herein. As illustrated in FIG. 7, the integrated NIR photonic and optical apparatus of embodiments of the subject invention, when combined with treatments involving MNPs, can enable applications such as, for example, imaging and on-demand drug targeting, brain cell specific gene delivery, and magnetized photo-biomodulation for treating various CNS disorders (e.g., for example, Alzheimer's, Parkinson's, neuroAIDS, drug addiction) or other disorders (e.g., diabetes, pulmonary and lung diseases, cardiovascular diseases) when applied in combination with different types of nanoparticles and/or nanocarriers.

The methods and processes described herein can be embodied as code and/or data. The software code and data described herein can be stored on one or more machine-readable media (e.g., computer-readable media), which may include any device or medium that can store code and/or data for use by a computer system. When a computer system and/or processer reads and executes the code and/or data stored on a computer-readable medium, the computer system and/or processer performs the methods and processes embodied as data structures and code stored within the computer-readable storage medium.

It should be appreciated by those skilled in the art that computer-readable media include removable and non-removable structures/devices that can be used for storage of information, such as computer-readable instructions, data structures, program modules, and other data used by a computing system/environment. A computer-readable medium includes, but is not limited to, volatile memory such as random access memories (RAM, DRAM, SRAM); and non-volatile memory such as flash memory, various read-only-memories (ROM, PROM, EPROM, EEPROM), magnetic and ferromagnetic/ferroelectric memories (MRAM, FeRAM), and magnetic and optical storage devices (hard drives, magnetic tape, CDs, DVDs); network devices; or other media now known or later developed that is capable of storing computer-readable information/data. Computer-readable media should not be construed or interpreted to include any propagating signals. A computer-readable medium of the subject invention can be, for example, a compact disc (CD), digital video disc (DVD), flash memory device, volatile memory, or a hard disk drive (HDD), such as an external HDD or the HDD of a computing device, though embodiments are not limited thereto. A computing device can be, for example, a laptop computer, desktop computer, server, cell phone, or tablet, though embodiments are not limited thereto.

MATERIALS AND METHODS

Synthesis of Magnetic Nanoparticles

The co-precipitation method was used for synthesis of magnetic nanoparticles (Ding, H. et al. Enhanced blood-brain barrier transmigration using a novel Transferrin-embedded fluorescent magnetoliposome nanoformulation. Nanotechnology 25, 055101-055101 (2014)). Briefly, 3 mL of $FeCl_3$ (0.487 g dissolved in 2 mol/L HCl) was thoroughly mixed in 10.33 mL of $H_2O$ and subsequent drop-by-drop addition of 2 mL $Na_2SO_3$ (0.126 g in 2 mL of water) to this solution was stir-mixed within a minute. Gradually the reaction solution turned from yellow to red-light yellow. 80 mL of ammonium hydroxide solution (0.80 $mol^{-1}$) was then added with vigorous stirring which lead to black precipitation. The solution was kept under continuous stirring for additional 30 minutes. The resultant MNPs crystals were washed and suspended in $H_2O$ which measured a pH of 7.5. The stability of MNPs was achieved by adjusting the pH to 3.0 and subsequent heating at 90° C. and 100° C. for 5 and 60 min, respectively. All processes were performed at room temperature.

Characterization of Magnetic Nanoparticles

Figure 8A:
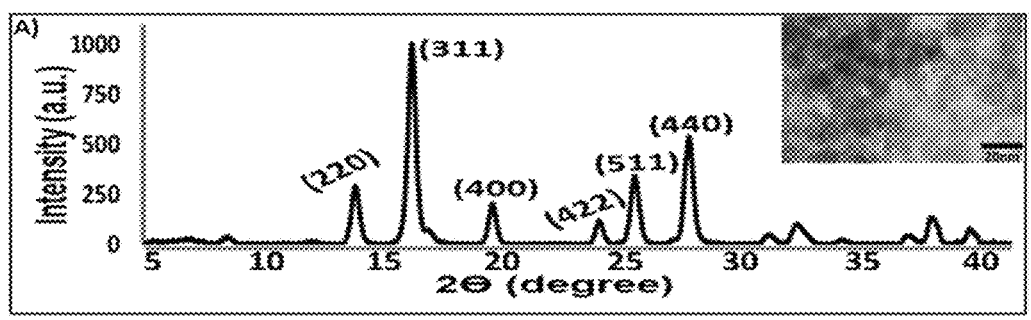
FIGS. 8A-8C demonstrate the characterization results of the MNPs.

Structural conformation of synthesized MNPs was verified using Bruker GADDS/D8 X-ray diffraction system with Apex Smart CCD Detector and Mo direct-drive rotating anode (50 kV; 20 mA). Diffraction patterns were analyzed and indexed using ICDD PDF 2015 database and Match software (FIG. 8A). Further, to confirm the elemental composition of MNPs, energy dispersive spectroscopy (EDS)

was conducted in a scanning electron microscope (JEOL JSM 5900LV) at 15 kV and working distance of 10 mm.

Figure 8B:
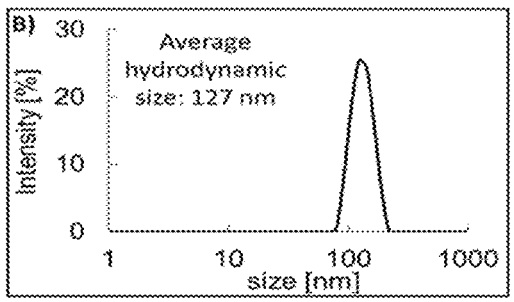
Figure 8C:
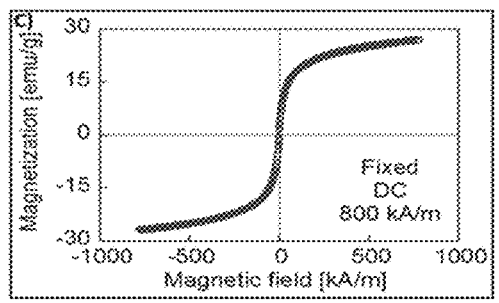

The hydrodynamic radius and size distribution of MNPs were analyzed using dynamic laser scattering (DLS) (90 Plus particle size analyzer, Brookhaven Instruments, USA) at room temperature (FIG. 8B). To examine the original crystal size, transmission electron microscopy (TEM) analysis was performed with the JEOL 1010 transmission electron microscope operated at 100 kV (FIG. 8A, inset). The magnetization curve of MNPs was measured using vibrating sample magnetometer (VSM-3, Toei Kogyo, Tokyo, Japan) equipped with an electromagnet (TEM-WFR7, Toei Kogyo, Tokyo, Japan) and a gaussmeter (Model 421, Lake Shore Cryotronics, Inc.) (FIG. 8C). The measurement was conducted at room temperature with a maximum field of 780 kA/m.

The Agilent 8453 UV-Visible Spectrometer with Quartz-1 cm path length was used for evaluating absorbance of MNPs from 200 to 1000 nm wavelength.

Cell Culture

SK-N-MC, a neuroepithelioma cell line derived from a metastatic supra-orbital human brain tumor, were cultured in minimum essential medium (MEM). MEM was supplemented with 10% fetal bovine serum (FBS), 100 U/mL penicillin, and 100 mg/ml streptomycin (Gibco-BRL, Gaithersburg, Md.). Cells were incubated at 37° C. in a 5% $CO_2$ incubator. Similarly, human primary astrocytes (HA) and CHME-5 human microglia cells were cultivated as per provider's recommendations.

NIR Exposure

NIR exposure was applied using a collimated NIR Laser Module source (RLDH808-1200-5, Roithner Laserthchnik Gmbh, Vienna, Austria) as described by Tang and McGoron (Tang, Y. & McGoron, A. J. Combined effects of laser-ICG photothermotherapy and doxorubicin chemotherapy on ovarian cancer cells. J Photochem Photobiol B 97, 138-144 (2009)). 808 nm of NIR with approximately 1.5 W/cm$^2$ of power density ("at-the-sample" power) was focused for 2 minutes on brain cells such as, for example, human primary astrocytes, SK-N-MC neuronal cells, and CHME-5 glia cells, cultured in 96-well plates in the presence or absence of MNPs (50 µg MNPs/mL). The fixed laser source had spot size of about 5 mm which covered approximately the central 80% cells of a well in the 96-well culture plates. Cells in the periphery of a well were exposed due to potential beam-spread upon the surface hitting of NIR during irradiation and as such, the whole well was illuminated. Cells were cultured in alternate wells so that potential cross-talk of NIR to a specific well was minimized for an adjacent well. Cells were pre-treated with MNPs 12 hours before NIR targeting. Temperature of a specific well was measured using a thermocouple (0.22 mm diameter) for the entire enduring of 2 minutes of NIR exposure.

Cell Viability Assay

The MTT (Thiazolyl blue tetrazolium bromide) cell proliferation assay was performed as described previously (Sagar, V. et al. Therapeutical Neurotargeting via Magnetic Nanocarrier: Implications to Opiate-Induced Neuropathogenesis and NeuroAIDS. J Biomed Nanotechnol 11, 1722-1733 (2015); Ding, H. et al. Enhanced blood-brain barrier transmigration using a novel Transferrin-embedded fluorescent magnetoliposome nanoformulation. Nanotechnology 25, 055101-055101 (2014); Pilakka-Kanthikeel, S Atluri, V. S. R., Sagar, V., Saxena, S. K. & Nair, M. Targeted Brain Derived Neurotropic Factors (BDNF) Delivery across the Blood-Brain Barrier for Neuro-Protection Using Magnetic Nano Carriers: An In-Vitro Study. PLoS ONE 8, e62241 (2013)).

Briefly, cells undergone NIR treatment were re-incubated at 37° C. for 3-6 hours in order to imitate a real-time situation where cells will be under the natural condition post NIR treatment. Cells from different experimental groups were given a 200 µL of media change with 20 µL of MTT solution added and gently rocked in the dark at room temperature for 2-3 hours. One volume of STOP solution containing 20% sodium dodecyl sulfate (SDS) in 50% dimethyl formamide was added to the rocking cell suspension in MTT solution and further gently rocked in the dark at room temperature for 1-2 hrs. The cell suspension was centrifuged at 2000 rpm for approximately 10 minutes and the supernatant was collected for the optical density determination of the solubilized formazan at 550 nm using Spectronic Genesys Bio10 spectrophotometer. The optical density of formazan in each treatment groups is directly proportional to the cell viability.

Cell Growth Resistance/Impedance ($\Omega$) Measurement

Astrocytes growth resistance/impedance was measured with the help of an electric cell-substrate impedance sensing instrument (model 1600RE, Applied Biophysics, USA) using 8W10E PET chips (Applied Biophysics), which contained 8 cell culture wells (Hondroulis, E., Zhang, Z., Chen, C. & Li, C.-Z. Impedance Based Nanotoxicity Assessment of Graphene Nanomaterials at the Cellular and Tissue Level. Analytical Letters 45, 272-282 (2011); Hondroulis, E., Liu, C. & Li, C. Z. Whole cell based electrical impedance sensing approach for a rapid nanotoxicity assay. Nanotechnology 21, 315103 (2011)). Each well of the chip contains 10 working electrodes (each 250 µm in diameter) embedded in parallel on a gold connection pad and all of the wells shared a common reference electrode. Astrocytes cultured with or without MNPs treatment were photo-targeted with NIR light and seeded in chip wells (5×104 cells/well). Both the working and the reference electrodes were connected to a phase-sensitive lock-in amplifier through a 1 M$\Omega$ resistor before an alternating current (AC) signal was applied. An electric potential of 1 V at 4 kHz was used for cell growth resistance measurements at 37° C. in a humidified incubator for up to 10 hours.

Confocal Microscopy and Characterization of Neuro-Spine Density

Membrane staining of neuronal cells for confocal microscopy and measurement of spine density was performed according to the method adopted from Atluri et al., 2014 (Atluri, V. S. et al. Vorinostat positively regulates synaptic plasticity genes expression and spine density in human immunodeficiency virus (HIV) infected neurons: role of nicotine in progression of HIV-associated neurocognitive disorder. Mol Brain 7, 37 (2014)). Cells were imaged using a TCS SP2 confocal laser scanning microscope (Leica Microsystems, Germany) at 488 nm using 60× oil immersion objectives and 2.5× confocal electronic zoom.

Biostatistical Analysis

Data in different figures are presented as mean±standard error of three experiments (n=3). Student's t-test was performed to compare means of two groups using GraphPad prism6 (San Diego, Ca) and P values 0.05 were considered as significant.

EXAMPLES

Following are examples that illustrate procedures for practicing the invention. These examples should not be construed as limiting.

Example 1—Effect of Short-Term MNPs-NIR Exposure on Temperature of Cell Culture Ambience NIR-based photonic and optical treatment in the presence of MNPs was achieved using the collimated NIR laser delivery system as shown in FIG. 1. As a first step towards assessing the efficacy of this approach for the brain region, the effect on temperature change of an in-vitro cell culture system upon short-term NIR light exposure (up to 2 minutes) was evaluated. The 808 nm NIR laser has been demonstrated to have superior CNS tissue penetration compared to light of other wavelengths such as 606 nm and 940 nm (Tedford, C. E., DeLapp, S., Jacques, S. & Anders, J. Quantitative analysis of transcranial and intraparenchymal light penetration in human cadaver brain tissue. Lasers Surg Med 47, 312-322 (2015)). As such, this wavelength was selected for the subsequent experiments.

The effect of NIR or MNPs-NIR on temperature of cell culture ambience of individual well was obtained by measuring the temperature difference at the beginning (0 second) and the end (120 seconds) of exposure. NIR exposure on cell culture system without MNPs showed a temperature rise of 0.46±0.152° C. and that of with MNPs showed an increase of 0.83±0.057° C. (*P<0.0177). Schematic in FIG. 1 shows the cell culture plate in the presence or absence of MNPs, which were homogenously exposed to 808 nm NIR with power of approximately 1.5 W/cm². Typical power intensities reported for NIR photonic and optical treatment range from 1 to about 100 W/cm² (Jaque, D. et al. Nanoparticles for photothermal therapies. Nanoscale 6, 9494-9530 (2015)). Because no previous reports suggest the combined use of MNPs and NIR for brain cells, a minimum recommended power density was selected considering higher physiological sensitivity of brain cells in compare to peripheral cells. To simulate the original cell culture condition, the temperature was maintained at 37° C. using the heated platform upon which the culture plates were placed during the NIR laser exposure and increase or decrease in temperature was measured using a thermocouple.

Figure 2:
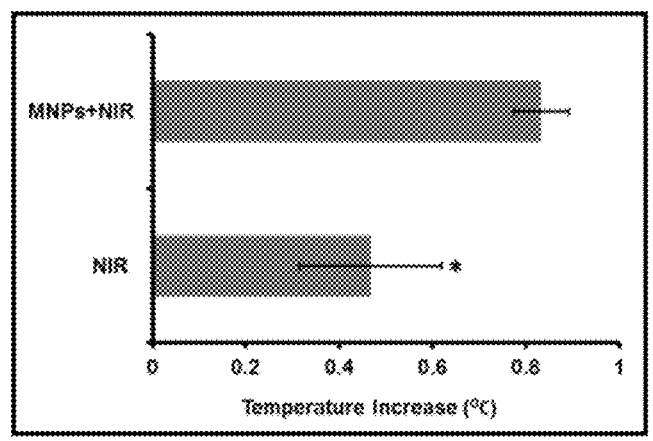
FIG. 2 shows a temperature profile of two sample cell cultures, one with and one without MNPs, as each culture was exposed to approximately 1.5 W/cm$^2$ of NIR for 2 minutes and the temperature of each culture was recorded by placing the thermocouple device at the bottom of the well throughout the exposure period.

As shown in FIG. 2, NIR laser exposure on the cell culture system without MNPs resulted in a temperature rise of 0.46±0.152° C. and that with MNPs resulted an increase of 0.83±0.057° C. MNPs absorption at 808 nm is near to bottom line, i.e. extremely low. Nonetheless, laser beam energy absorbed by the components of cell-culture media may also have added to the 0.46° C. temperature rise in the absence of MNPs. Thus, the net temperature rise upon NIR laser exposure in the presence of MNPs is only 0.37±0.115° C. which is insignificant in terms of hyperthermia generation and can be used in vivo.

Example 2—Effect of Short-Term MNPs-NIR Exposure on Brain Cell Viability

Figure 3:
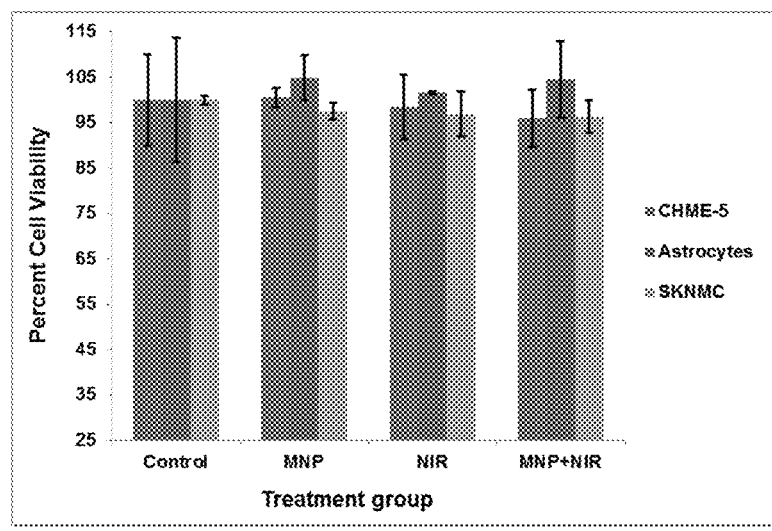
FIG. 3 demonstrates percent cell viability of three major types of brain cells including human primary astrocytes, SK-N-MC human neuroepithelioma cells, and CHME-5 human microglia cell lines. The cell viability was obtained by using a Thiazolyl blue tetrazolium bromide (MTT) cytotoxicity assay.

In order to assess the potential use for the brain region, the nonspecific cytotoxicity of this novel MNPs-NIR during short-time (e.g., for 2 minutes) treatment to three major brain cells, namely, human primary astrocytes, SK-N-MC human neuroepithelioma cells, and CHME-5 human microglia cells was evaluated. The results of quantitative cell cytotoxicity determined by the MTT cell proliferation assay showed that MNPs-NIR exposure was not toxic to any of the brain cell types used in this study (FIG. 3).

MNPs alone did not deter the cell viability of Human primary astrocytes, SK-N-MC human neuroepithelioma cells or CHME-5 human microglia cells. NIR light with 800 nm to 1000 nm of wavelength can be transmitted across tissue without inducing any damage to cellular macromolecules or organelles. As such, similar to the MNPs-alone treatment, cell viability is expected to remain unaltered upon exposure of NIR. Percent cell viability in the case of NIR-alone experiment was 98.45±7.05, 101.58±0.36, and 96.90±4.85 for CHME-5 human microglia cells, human primary astrocytes, and SK-N-MC human neuroepithelioma cells, respectively.

Similar to this result, it has been shown previously that 808 nm irradiation on Eca-109 cells for 20 minutes did not change their viability (Shi, D., Sadat, M. E., Dunn, A. W. & Mast, D. B. Photo-fluorescent and magnetic properties of iron oxide nanoparticles for biomedical applications. Nanoscale 7, 8209-8232 (2015)). Shen et al. (2015) also showed the same for the A549 cells which were exposed to an NIR laser of 808 nm in wavelength and 5 W/cm² in power density in the presence or absence of individually dispersed MNPs for 3 minutes (Shen, S. et al. Magnetic nanoparticle clusters for photothermal therapy with near-infrared irradiation. Biomaterials 39, 67-74 (2015)). As shown in FIG. 3, percent cell viability in the case of MNP-NIR treatment was 96.00±6.25, 104.58±8.40, and 96.35±3.64 for CHME-5 human microglia cells, Human primary astrocytes and SKNMC human neuroepithelioma cells, respectively.

The unaffected cell viability either during NIR-alone or MNPs-NIR exposure (FIG. 3) coincides with the insignificant temperature rise of the culture system (FIG. 2). In fact, studies pertaining to the oncolytic effect of MNP-NIR exposure report that the cytotoxic effect is induced when the local temperature rise is greater than 42° C. (Parton, E., Palma, R. D. & Borghs, G. Biomedical applications using magnetic nanoparticles, (2008); Zhu, C.-H., Lu, Y., Peng, J., Chen, J.-F. & Yu, S.-H. Photothermally Sensitive Poly(N-isopropylacrylamide)/Graphene Oxide Nanocomposite Hydrogels as Remote Light-Controlled Liquid Microvalves. Advanced Functional Materials 22, 4017-4022 (2012)).

The "no-effect" exhibition of cell viability demonstrated herein may also be due to the low light absorption by the natural endogenous cytochromes of cells upon short-term exposure, which may cause minimal temperature elevation accounting to the high cell survivability (Shen, S. et al. Magnetic nanoparticle clusters for photothermal therapy with near-infrared irradiation. Biomaterials 39, 67-74 (2015)). Advantageously, the unaffected percent cell viability potentiates the safe use of short-term MNP-NIR exposure for biomedical applications in the brain region.

Example 3—Effect of Short-Term MNPs-NIR Exposure on Brain Cell Growth Behavior While the MTT cell proliferation assay provides a general sense of cytotoxicity at a final time point after specific duration of treatment, analyzing the continuous growth behavior of cells over time may reveal kinetic effects of toxicity (Medeiros, S. F., Santos, A. M., Fessi, H. & Elaissari, A. Stimuli-responsive magnetic particles for biomedical applications. Int J Pharm 403, 139-161, doi:10.1016/j.ijpharm.2010.10.011 (2011); Bansal, A. & Zhang, Y. Photocontrolled Nanoparticle Delivery Systems for Biomedical Applications. Accounts of Chemical Research 47, 3052-3060 (2014)). Furthermore, astrocytes growth resistance/impedance was measured for 10 hours post-treatment using the electric cell-substrate impedance sensing method. This method measures the resistance (1) produced by growing cell monolayers over the electrodes and can detect changes in resistance to AC current flow that may occur with changes in the cell layer (Hondroulis, E., Zhang, Z., Chen, C. & Li, C.-Z. Impedance Based Nanotoxicity Assessment of Graphene Nanomaterials at the Cellular and Tissue Level. Analytical Letters 45, 272-282 (2011); Hondroulis, E., Liu, C. & Li, C. Z. Whole cell based electrical impedance sensing approach for a rapid nanotoxicity assay. Nanotechnology 21, 315103 (2011)). Primarily, growth resistance of each treatment group was compared with resistance of blank well containing culture media to obtain blank-normalized resistance value.

Figure 4:
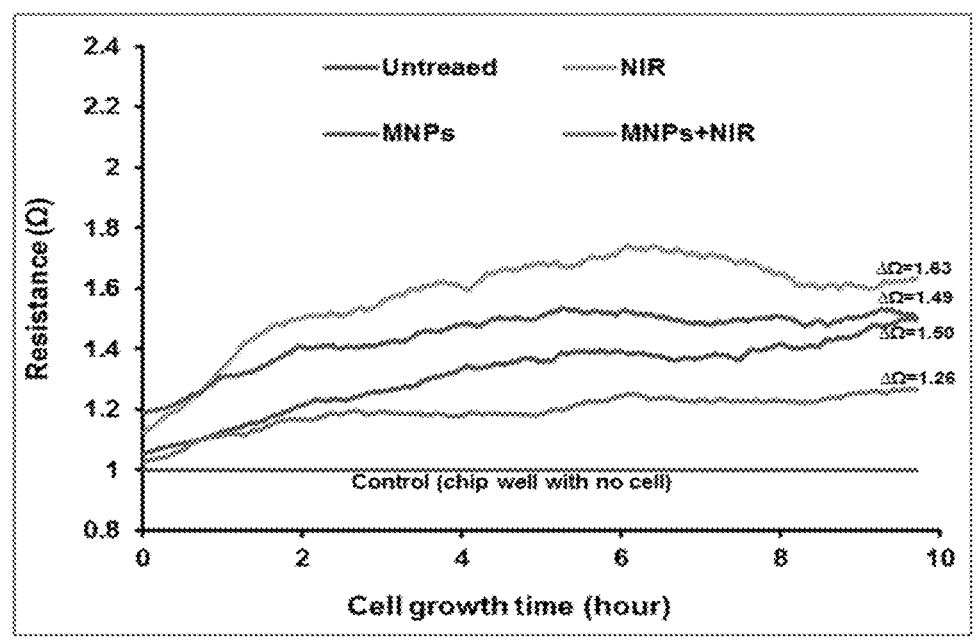
FIG. 4 shows cell growth behavior of human primary astrocytes over 10 hours of culturing period by measuring the growth-resistance ($\Omega$) kinetics of the astrocytes with various treatments. The end-point blank-normalized resistance ($\Delta\Omega$) values were 1.63, 1.49, 1.26, and 1.50 for the NIR treatment, the MNPs-alone treatment, the MNPs and NIR treatment, and the untreated control exposure, respectively. These values being in the same range suggests that similar cell growth behavior was observed during all treatment types.

As shown in FIG. 4, growth-resistance kinetics of astrocytes with all kinds of treatments showed a steady upward slope. The end point blank-normalized resistance ($\Delta\Omega$) value after 10 hours of culture was 1.63, 1.49, 1.26, and 1.50 for NIR-alone treatment, MNPs-alone treatment, MNPs-NIR, and untreated control exposure, respectively. Since the cell growth-resistances values were in the same range, a similar growth behavior of attached cells across all groups is evident.

The presence of MNPs on the electrode surface of the culture chip may result in a slower cellular attachment process; however, in a real in-vivo scenario the effect on the cellular attachment process due to MNPs may be inconsequential. Moreover, the intrinsic AC properties of MNPs may also interfere with the AC current flow of the culture chip electrodes and subsequently may obstruct the cell growth-resistance measurement. These factors may have resulted in a relatively slower kinetic slope in MNPs-only and MNPs-NIR treated cells than the NIR-only and untreated control groups. A little up or down slope of the growth kinetics among groups is expected during the early hour due to variations in the cell attachment rate which can be influenced by many other factors such as initial cell density, cellular transitory metabolic slowdown due to treatment effects, etc. (Hondroulis, E., Zhang, Z., Chen, C. & Li, C.-Z. Impedance Based Nanotoxicity Assessment of Graphene Nanomaterials at the Cellular and Tissue Level. Analytical Letters 45, 272-282 (2011); Hondroulis, E., Liu, C. & Li, C. Z. Whole cell based electrical impedance sensing approach for a rapid nanotoxicity assay. Nanotechnology 21, 315103 (2011)). Thus, a longer monitoring of cell growth-behavior via the resistance/impedance sensing method may reflect a healthy cellular status and factors such as cell attachment and metabolic pause can be nullified. Nonetheless, the astrocytes growth-resistance pattern obtained for the initial 10 hrs is in accordance with the MTT assay (FIG. 3) suggesting no harmful effect of short-term MNPs-NIR exposure on cell health.

Example 4—Effect of Short-Term MNPs-NIR Exposure on Brain Cell Plasticity

Long-term effect of MNPs-NIR treatment on dendrite and spine morphology (synaptic plasticity) of SK-N-MC cells was also monitored. Spine morphology plays an important role in maximizing the effectiveness of the synaptic transmission in brain and to the periphery (Sagar, V. et al. Therapeutical Neurotargeting via Magnetic Nanocarrier: Implications to Opiate-Induced Neuropathogenesis and NeuroAIDS. J Biomed Nanotechnol 11, 1722-1733 (2015); Atluri, V. S. et al. Vorinostat positively regulates synaptic plasticity genes expression and spine density in HIV infected neurons: role of nicotine in progression of HIV-associated neurocognitive disorder. Mol Brain 7, 37 (2014)). Treated or untreated cells were allowed to grow on cover slip for more than 72 hours such that homogenous elongation of dendritic and spinal projections can take place. Subsequently, cells were phosphate-buffered saline (PBS)-fixed and stained using the green-fluorescent membrane tracer 1,1'-Dioctadecyl-3, 3,3,3-tetramethylindocarbocyanine perchlorate. This lipophilic dye uniformly labeled lipid contents of plasma membrane via lateral diffusion. The stained cells on slides were now microscoped for confocal imaging. The 60× immersion objectives lens at 488 nm illusion and 2.5× electronic zoom provided the required magnification to visualize dendritic spine of individual cells. Spine density were quantified using obtained confocal images using a well-established protocol (Sagar, V. et al. Therapeutical Neurotargeting via Magnetic Nanocarrier: Implications to Opiate-Induced Neuropathogenesis and NeuroAIDS. J Biomed Nanotechnol 11, 1722-1733 (2015); Atluri, V. S. et al. Vorinostat positively regulates synaptic plasticity genes expression and spine density in HIV infected neurons: role of nicotine in progression of HIV-associated neurocognitive disorder. Mol Brain 7, 37 (2014); Pilakka-Kanthikeel, S., Atluri, V. S. R., Sagar, V., Saxena, S. K. & Nair, M. Targeted Brain Derived Neurotropic Factors (BDNF) Delivery across the Blood-Brain Barrier for Neuro-Protection Using Magnetic Nano Carriers: An In-Vitro Study. PLoS ONE 8, e62241 (2013)) where ImageJ software was used to measure defined length of single cells and number of spines present within that length is counted (spine density=number of spines/dendritic or cell length).

Figure 5A:
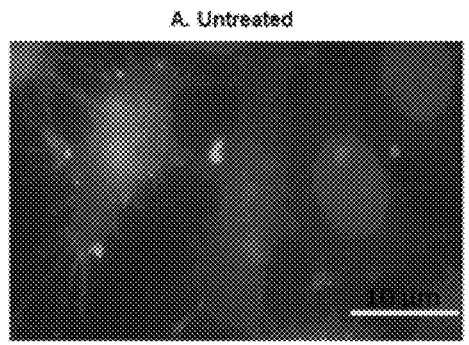
FIGS. 5A-5D shows the confocal microscopic imaging results evaluating the dendrite and spine morphology (synaptic plasticity) of SK-N-MC cells after 72 hours of NIR treatment in the absence (5C) or presence (5D) of MNPs in comparison to the control (5A) and the MNP-treated sample (5B). Healthy dendritic and spine morphology of SK-N-MC cells was evident for all treatments.
Figure 5B:
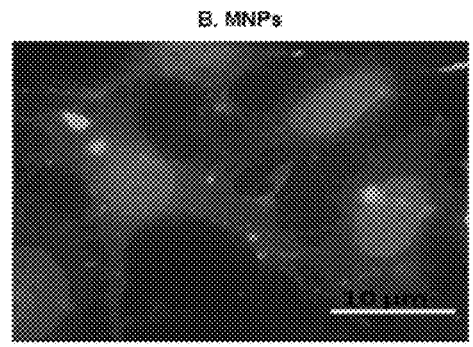
Figure 5C:
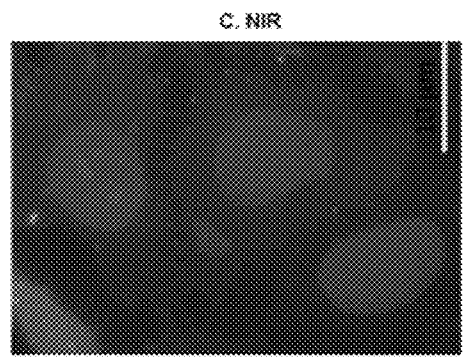
Figure 5D:
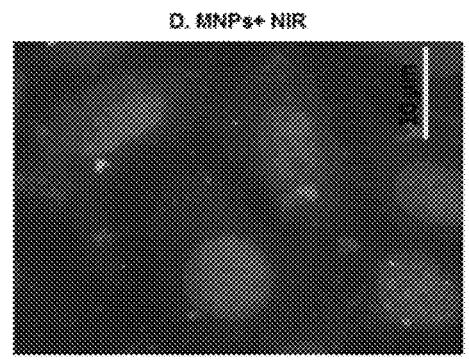
Figure 6:
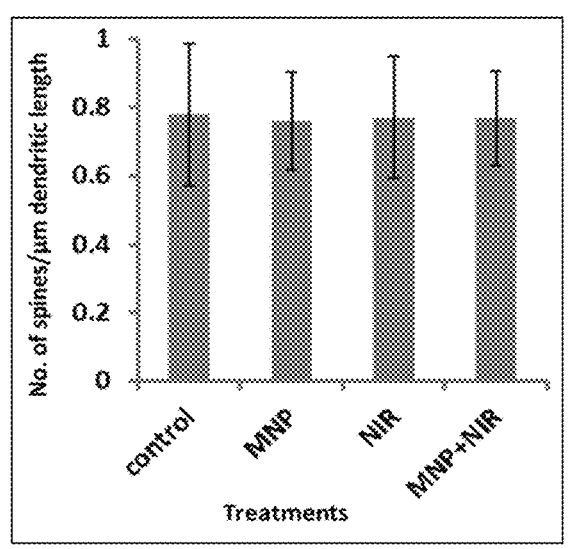
FIG. 6 shows the spinal density (i.e., the number of spines per 1 μm in dendritic length) of SK-N-MC. Spine density remains unchanged in all treatments including the untreated control (0.77±0.20 per μm$^2$), treated with MNPs (0.76±0.14 per μm$^2$), treated with NIR (0.76±0.13 per μm$^2$), and treated with MNPs+NIR (0.77±0.17 per μm$^2$), suggesting that the coupling of transient near infrared photonic with magnetic nanoparticles has no adverse effect on brain cell growth and behaviors.

As shown from confocal microscopy analysis in FIGS. 5A-5D and FIG. 6, healthy dendritic and spine morphology of SK-N-MC cells is evident for all treatments. NIR-treated cells with and without MNPs showed a spinal density of 0.76±0.13 and 0.77±0.17 per $\mu m^2$, respectively, whereas that of the untreated cells was approximately 0.77±0.20 per $\mu m^2$ (FIG. 6). Cells treated with MNPs only showed a spinal density of 0.76±0.14 per $\mu m^2$ (FIG. 6).

As shown in FIG. 5B, MNPs alone did not affect the dendritic and spinal elongation (Sagar, V. et al. Therapeutical Neurotargeting via Magnetic Nanocarrier: Implications to Opiate-Induced Neuropathogenesis and NeuroAIDS. J Biomed Nanotechnol 11, 1722-1733 (2015); Pilakka-Kanthikeel, S., Atluri, V. S. R., Sagar, V., Saxena, S. K. & Nair, M. Targeted Brain Derived Neurotropic Factors (BDNF) Delivery across the Blood-Brain Barrier for Neuro-Protection Using Magnetic Nano Carriers: An In-Vitro Study. PLoS ONE 8, e62241 (2013)). Similarly, NIR-alone (FIG. 5C) and MNPs-NIR (FIG. 5D) treated cells showed dendritic and spinal morphology comparable to that of untreated controls (FIG. 5A). Thus, healthy synaptic plasticity was observed in all experimental groups. This result further substantiates the observations that short-term MNPs-NIR exposures do not affect brain cell growth and behaviors.

Example 5—Applications of the MNP-NIR Treatment

FIG. 7 illustrates a schematic of employing the NIR apparatus (with a transient NIR source) provided herein in combination with MNP treatment for non-invasive targeting, release, and monitoring of drugs or other active agents to CNS tissues.

Specifically, an in silico-controlled, non-invasive magnetic force can drive MNPs across the blood-brain barrier (BBB) and an NIR apparatus can simultaneously apply phototargeting to cause the release of drugs or active agents bound to the MNPs, which are further encapsulated in hydrogel and/or liposomes sensitive to the stimulation of NIR. This mechanism is possible because transitory opto-electronic excitation-mediated molecular vibrations on MNPs surfaces, even for short-term NIR laser exposure, can change the charge distribution of the MNPs' surfaces and subsequently breaking the intermolecular bonds between drugs or active agents and the MNPs.

It should be understood that the examples and embodiments described herein are for illustrative purposes only and that various modifications or changes in light wavelengths and types of nanoparticles thereof will be suggested to persons skilled in the art and are to be included within the spirit and purview of this application.

All patents, patent applications, provisional applications, and publications referred to or cited herein (including those in the "References" section, if present) are incorporated by reference in their entirety, including all figures and tables, to the extent they are not inconsistent with the explicit teachings of this specification.

REFERENCES

1. Gu, L., Koymen, A. R. & Mohanty, S. K. (2014). Crystalline magnetic carbon nanoparticle assisted photothermal delivery into cells using CW near-infrared laser beam. Sci. Rep. 4, 5106.
2. Wang, H., Cao, G., Gai, Z., Hong, K., Banerjee, P., and Zhou, S. (2015). Magnetic/NIR-responsive drug carrier, multicolor cell imaging, and enhanced photothermal therapy of gold capped magnetite-fluorescent carbon hybrid nanoparticles. Nanoscale, 7, 7885-7895.
3. Maier-Hauff, K., Ulrich, F., Nestler, D., Niehoff, H., Wust, P., Thiesen, B., Orawa, H., Budach, V., and Jordan., A. (2011) Efficacy and safety of intratumoral thermotherapy using magnetic iron-oxide nanoparticles combined with external beam radiotherapy on patients with recurrent glioblastoma multiforme. J Neurooncol, 103:317-324.
4. Zhu, C.-H., Lu, Y., Peng, J., Chen, J.-F., and Yu, S.-H. (2012). Photothermally sensitive poly(N-isopropylacrylamide)/graphene oxide nanocomposite hydrogels as remote light-controlled liquid microvalves, Adv. Funct. Mater., 22, 4017-4022.
5. Yan, B., Boyer, J. C., Habault, D., Branda, N. R. & Zhao, Y. (2012). Near Infrared Light Triggered Release of Biomacromolecules from Hydrogels Loaded with Upconversion Nanoparticles. J. Am. Chem. Soc. 134, 16558-16561.
6. You, J., Zhang, P., Hu, F., Du, Y., Yuan, H., Zhu, J., Wang, Z., Zhou, J., and Li, Chun. (2014) Near-infrared light-sensitive liposomes for the enhanced photothermal tumor treatment by the combination with chemotherapy. Pharm. Res., 31: pp. 554-565.
7. Chu, M., Shao, Y., Peng, J., Dai, X., Li, H., Wu, Q., and Shi, D. (2013) Near-infrared laser light mediated cancer therapy by photothermal effect of Fe3O4 magnetic nanoparticles. Biomaterials, 34, pp. 4078-4088.
8. Fusco, S., Sakar, M. S., Kennedy, S., Peters, C., Bottani, R., Starsich, F., Mao, A., Sotiriou, G. A., Pane, S., Pratsinis, S. E., Mooney, D., and Nelson, B. (2014). An Integrated Microrobotic Platform for On-Demand, Targeted Therapeutic Interventions. Adv. Mater., 26, 952-957.
9. Nagai, et al. (US 20120032147 A1) Biological component detection device
10. Gerbier, et al. (US 20110267681 A1) Optical wavelength conversion device, and coherent light source using same
11. Kitagawa (US 20040061073 A1) Laser scanning microscope, semiconductor laser light source unit, scanning unit for a laser scanning microscope, and method of connecting semiconductor light source to scanning microscope
12. Mizuuchi (US 20070053388 A1) Coherent light source and optical device
13. Lee, et al. (US 20070078310 A1) Apparatus and method for measuring biological information
14. Oraevsky, et al. (US 20080160090 A1) Laser-activated nanothermolysis of cells
15. Fernandez, et al. (U.S. Pat. No. 5,818,582) Apparatus and method for phase fluorometry
16. Sevick-Muraca, et al. (U.S. Pat. No. 5,865,754) Fluorescence imaging system and method
17. Kobayashi, et al. (U.S. Pat. No. 6,415,236) Apparatus for determining concentrations of hemoglobins
18. Bouzid (U.S. Pat. No. 6,449,039) Laser scanning fluorescence microscopy with compensation for spatial dispersion of fast laser pulses
19. Hofmann-Amtenbrink, M., Von Rechenberg, B. & Hofmann, H. in *Nanostructured Materials for Biomedical Application* (ed M.C. Tan) 119-149 (Transworld Research Network, 2009).
20. Sagar, V., Pilakka-Kanthikeel, S., Pottathil, R., Saxena, S. K. & Nair, M. Towards nanomedicines for neuroAIDS. Rev Med Virol 24, 103-124, doi:10.1002/rmv.1778 (2014).
21. Santoso, M. R. & Yang, P. C. Magnetic Nanoparticles for Targeting and Imaging of Stem Cells in Myocardial Infarction. Stem Cells Int 2016, 4198790, doi:10.1155/2016/4198790 (2016).
22. Parton, E., Palma, R. D. & Borghs, G. Biomedical applications using magnetic nanoparticles, 2008).
23. Unsoy, G. & Gunduz, U. Targeted silencing of Survivin in cancer cells by siRNA loaded chitosan magnetic nanoparticles. Expert Rev Anticancer Ther, 1-9, doi:10.1080/14737140.2016.1184981 (2016).
24. Laurent, S., Saei, A. A., Behzadi, S., Panahifar, A. & Mahmoudi, M. Superparamagnetic iron oxide nanoparticles for delivery of therapeutic agents: opportunities and challenges. Expert Opin Drug Deliv 11, 1449-1470, doi: 10.1517/17425247.2014.924501 (2016).
25. Valdiglesias, V. et al. Are iron oxide nanoparticles safe? Current knowledge and future perspectives. J Trace Elem Med Biol, doi: 10.1016/j.jtemb.2016.03.017 (2016).
26. Long, N. V. et al. Biomedical Applications of Advanced Multifunctional Magnetic Nanoparticles. J Nanosci Nanotechnol 15, 10091-10107 (2015).
27. Wiogo, H. T. R. et al. Insight into Serum Protein Interactions with Functionalized Magnetic Nanoparticles in Biological Media. Langmuir 28, 4346-4356, doi: 10.1021/la204740t (2012).
28. Benede, J. L., Chisvert, A., Giokas, D. L. & Salvador, A. Development of stir bar sorptive-dispersive microextraction mediated by magnetic nanoparticles and its analytical application to the determination of hydrophobic organic compounds in aqueous media. J Chromatogr A 1362, 25-33, doi: 10.1016/j.chroma.2014.08.024 (2006).
29. Ghose, S. K. et al. in Developments in Earth and Environmental Sciences Vol. Volume 7 1-29 (Elsevier, 2007).

30. Sagar, V. et al. Therapeutical Neurotargeting via Magnetic Nanocarrier: Implications to Opiate-Induced Neuropathogenesis and NeuroAIDS. J Biomed Nanotechnol 11, 1722-1733 (2015).
31. Ding, H. et al. Enhanced blood-brain barrier transmigration using a novel Transferrin-embedded fluorescent magnetoliposome nanoformulation. Nanotechnology 25, 055101-055101, doi:10.1088/0957-4484/25/5/055101 (2014).
32. Shen, S. et al. Magnetic nanoparticle clusters for photothermal therapy with near-infrared irradiation. Biomaterials 39, 67-74, doi: 10.1016/j.biomaterials.2014.10.064 (2015).
33. Jain, T. K., Reddy, M. K., Morales, M. A., Leslie-Pelecky, D. L. & Labhasetwar, V. Biodistribution, clearance, and biocompatibility of iron oxide magnetic nanoparticles in rats. Mol Pharm 5, 316-327, doi:10.1021/mp7001285 (2008).
34. Mura, S., Nicolas, J. & Couvreur, P. Stimuli-responsive nanocarriers for drug delivery. Nat Mater 12, 991-1003, doi:10.1038/nmat3776 (2013).
35. Reineke, T. M. Stimuli-Responsive Polymers for Biological Detection and Delivery. ACS Macro Letters 5, 14-18, doi:10.1021/acsmacrolett.5b00862 (2016).
36. Medeiros, S. F., Santos, A. M., Fessi, H. & Elaissari, A. Stimuli-responsive magnetic particles for biomedical applications. Int J Pharm 403, 139-161, doi:10.1016/j.ijpharm.2010.10.011 (2011).
37. Bansal, A. & Zhang, Y. Photocontrolled Nanoparticle Delivery Systems for Biomedical Applications. Accounts of Chemical Research 47, 3052-3060, doi:10.1021/ar500217w (2014).
38. Kim, H., Chung, K., Lee, S., Kim, D. H. & Lee, H. Near-infrared light-responsive nanomaterials for cancer theranostics. Wiley Interdiscip Rev Nanomed Nanobiotechnol 8, 23-45, doi:10.1002/wnan.1347 (2016).
39. Gu, L., Koymen, A. R. & Mohanty, S. K. Crystalline magnetic carbon nanoparticle assisted photothermal delivery into cells using CW near-infrared laser beam. Scientific Reports 4, 5106 (2014).
40. Wang, H. et al. Magnetic/NIR-responsive drug carrier, multicolor cell imaging, and enhanced photothermal therapy of gold capped magnetite-fluorescent carbon hybrid nanoparticles. Nanoscale 7, 7885-7895, doi: 10.1039/c4nr07335e (2015).
41. Zhu, C.-H., Lu, Y., Peng, J., Chen, J.-F. & Yu, S.-H. Photothermally Sensitive Poly(N-isopropylacrylamide)/Graphene Oxide Nanocomposite Hydrogels as Remote Light-Controlled Liquid Microvalves. Advanced Functional Materials 22, 4017-4022, doi:10.1002/adfm.201201020 (2012).
42. Yan, B., Boyer, J. C., Habault, D., Branda, N. R. & Zhao, Y. Near infrared light triggered release of biomacromolecules from hydrogels loaded with upconversion nanoparticles. J Am Chem Soc 134, 16558-16561, doi: 10.1021/ja308876j (2012).
43. Fusco, S. et al. An integrated microrobotic platform for on-demand, targeted therapeutic interventions. Adv Mater 26, 952-957, doi:10.1002/adma.201304098 (2014).
44. You, J. et al. Near-infrared light-sensitive liposomes for the enhanced photothermal tumor treatment by the combination with chemotherapy. Pharm Res 31, 554-565, doi:10.1007/s11095-013-1180-7 (2014).
45. Tao, W., Wilkinson, J., Stanbridge, E. J. & Berns, M. W. Direct gene transfer into human cultured cells facilitated by laser micropuncture of the cell membrane. Proceedings of the National Academy of Sciences of the United States of America 84, 4180-4184 (1987).
46. Schneckenburger, H., Hendinger, A., Sailer, R., Strauss, W. S. & Schmitt, M. Laser-assisted optoporation of single cells. J Biomed Opt 7, 410-416, doi:10.1117/1.1485758 (2002).
47. Palumbo, G. et al. Targeted gene transfer in eucaryotic cells by dye-assisted laser optoporation. J Photochem Photobiol B 36, 41-46, doi:10.1016/S1011-1344(96) 07335-6 (1996).
48. Liu, B. et al. Functional nanomaterials for near-infrared-triggered cancer therapy. Biomater Sci 4, 890-909, doi: 10.1039/c6bm00076b (2016).
49. Mohanty, S., Sharma, M. & Gupta, P. Laser-assisted microinjection into targeted animal cells. Biotechnology Letters 25, 895-899 (2003).
50. Hosokawa, Y. et al. Gene delivery process in a single animal cell after femtosecond laser microinjection. Applied Surface Science 255, 9880-9884, doi:http://dx.doi.org/10.1016/j.apsusc.2009.04.111 (2009).
51. Stracke, F., Rieman, I. & Konig, K. Optical nanoinjection of macromolecules into vital cells. Journal of photochemistry and photobiology. B, Biology 81, 136-142, doi:10.1016/j.jphotobiol.2005.07.006 (2005).
52. Schinkel, H., Jacobs, P., Schillberg, S. & Wehner, M. Infrared picosecond laser for perforation of single plant cells. Biotechnol Bioeng 99, 244-248, doi:10.1002/bit.21549 (2008).
53. Sordillo, L. A., Pu, Y., Pratavieira, S. o., Budansky, Y. & Alfano, R. R. Deep optical imaging of tissue using the second and third near-infrared spectral windows. Journal of Biomedical Optics 19, 056004-056004 (2014).
54. Tirlapur, U. K. & Konig, K. Targeted transfection by femtosecond laser. Nature 418, 290-291, doi:10.1038/418290a (2002).
55. Chu, M. et al. Near-infrared laser light mediated cancer therapy by photothermal effect of Fe3O4 magnetic nanoparticles. Biomaterials 34, 4078-4088, doi:10.1016/j.biomaterials.2013.0.01.086 (2013).
56. Rudolf, H., Silvio, D., Robert, M. 1. & Matthias, Z. Magnetic particle hyperthermia: nanoparticle magnetism and materials development for cancer therapy. Journal of Physics: Condensed Matter 18, 52919 (2006).
57. Maier-Hauff, K. et al. Efficacy and safety of intratumoral thermotherapy using magnetic iron-oxide nanoparticles combined with external beam radiotherapy on patients with recurrent glioblastoma multiforme. Journal of Neuro-Oncology 103, 317-324, doi:10.1007/s11060-010-0389-0 (2011).
58. Tang, Y. & McGoron, A. J. Combined effects of laser-ICG photothermotherapy and doxorubicin chemotherapy on ovarian cancer cells. J Photochem Photobiol B 97, 138-144, doi:10.1016/j.jphotobiol.2009.09.001 (2009).
59. Pilakka-Kanthikeel, S., Atluri, V. S. R., Sagar, V., Saxena, S. K. & Nair, M. Targeted Brain Derived Neurotropic Factors (BDNF) Delivery across the Blood-Brain Barrier for Neuro-Protection Using Magnetic Nano Carriers: An In-Vitro Study. PLoS ONE 8, e62241 (2013).
60. Hondroulis, E., Zhang, Z., Chen, C. & Li, C.-Z. Impedance Based Nanotoxicity Assessment of Graphene Nanomaterials at the Cellular and Tissue Level. Analytical Letters 45, 272-282, doi:10.1080/00032719.2011.633184 (2011).
61. Hondroulis, E., Liu, C. & Li, C. Z. Whole cell based electrical impedance sensing approach for a rapid nanotoxicity assay. Nanotechnology 21, 315103, doi:10.1088/0957-4484/21/31/315103 (2011).

62. Atluri, V. S. et al. Vorinostat positively regulates synaptic plasticity genes expression and spine density in HIV infected neurons: role of nicotine in progression of HIV-associated neurocognitive disorder. Mol Brain 7, 37, doi:10.1186/1756-6606-7-37 (2014).
63. Sun, Y.-k., Ma, M., Zhang, Y. & Gu, N. Synthesis of nanometer-size maghemite particles from magnetite. Colloids and Surfaces A: Physicochemical and Engineering Aspects 245, 15-19, doi:10.1016/j.colsurfa.2004.05.009 (2004).
64. Liu, J., Wen, J., Zhang, Z., Liu, H. & Sun, Y. Voyage inside the cell: Microsystems and nanoengineering for intracellular measurement and manipulation. Microsystems & Nanoengineering 1, 15020 (2015).
65. Saiyed, Z. M., Gandhi, N. H. & Nair, M. P. Magnetic nanoformulation of azidothymidine 5′-triphosphate for targeted delivery across the blood-brain barrier. Int J Nanomedicine 5, 157-166 (2010).
66. Shi, D., Sadat, M. E., Dunn, A. W. & Mast, D. B. Photo-fluorescent and magnetic properties of iron oxide nanoparticles for biomedical applications. Nanoscale 7, 8209-8232, doi:10.1039/c5nr01538c (2015).

What is claimed is:

1. An apparatus comprising:
a light source;
a cell culture plate configured to fix thereon a biological sample;
a sample stage having fixed thereon the cell culture plate and configured to provide heat to adjust a temperature of the sample;
a microscope apparatus capable of capturing and processing real-time images of the sample as it is subjected to the light emitted from the light source, the microscope apparatus comprising a microscope selected from an electron microscope and a scanning probe microscope;
a temperature-sensing device connected to the sample stage and measuring a temperature of the sample stage;
a magnetic coil configured to provide the sample stage with a magnetic force; and
an optical fiber connecting the light source to the microscope apparatus,
the light source and the microscope being disposed above the same top surface of the sample stage, and the light source being configured such that it serves as an incident light of the microscope,
the magnetic coil being disposed below the sample stage,
the temperature-sensing device being configured to monitor the real-time temperature of the sample as it is fixed on or with the sample stage,
the temperature-sensing device being selected from a thermometer, a thermistor, and a thermocouple,
the light source being positioned to directly face an upper surface of the cell culture plate,
the microscope apparatus further comprising computer hardware and software capable of capturing and processing real-time images of the biological sample, and
the light source being a near-infrared (NIR) light source, and the NIR light of the NIR light source having a wavelength in a range of from 700 nm to 1000 nm, and the NIR light having a power density in a range of from 1 W/cm$^2$ to 10 W/cm$^2$.

2. The apparatus according to claim 1, the biological sample comprising brain cells selected from human primary astrocytes, SK-N-MC human neuroepithelioma cells, CHME-5 human microglia cells, and a combination thereof.

3. The apparatus according to claim 1, the light source emitting intermittent light waves.

4. The apparatus according to claim 1, the light source emitting continuous light waves.

5. The apparatus according to claim 1, the temperature-sensing device being a thermocouple.

6. The apparatus according to claim 1, the biological sample being a sample treated with magnetic nanoparticles encapsulated by a light sensitive material.

* * * * *